US012605375B2

(12) United States Patent
Zhang et al.

(10) Patent No.: US 12,605,375 B2
(45) Date of Patent: Apr. 21, 2026

(54) USE OF CSF-1R KINASE INHIBITOR

(71) Applicants: Shanghai Runshi Medical Technology Co., Ltd, Shanghai (CN); Shanghai Institute of Materia Medica, Chinese Academy of Sciences, Shanghai (CN)

(72) Inventors: Ao Zhang, Shanghai (CN); Meiyu Geng, Shanghai (CN); Jing Ai, Shanghai (CN); Caixia Wang, Shanghai (CN); Xia Peng, Shanghai (CN); Yang Zhang, Shanghai (CN); Jian Ding, Shanghai (CN)

(73) Assignees: Shanghai Runshi Medical Technology Co., Ltd, Shanghai (CN); Shanghai Institute of Materia Medica, Chinese Academy of Sciences, Shanghai (CN)

( * ) Notice: Subject to any disclaimer, the term of this patent is extended or adjusted under 35 U.S.C. 154(b) by 832 days.

(21) Appl. No.: 17/802,898

(22) PCT Filed: Feb. 26, 2021

(86) PCT No.: PCT/CN2021/078098

§ 371 (c)(1),
(2) Date: Aug. 26, 2022

(87) PCT Pub. No.: WO2021/170078

PCT Pub. Date: Sep. 2, 2021

(65) Prior Publication Data

US 2023/0285389 A1 Sep. 14, 2023

(30) Foreign Application Priority Data

Feb. 28, 2020 (CN) ........................ 202010128115.4

(51) Int. Cl.
*A61K 31/496* (2006.01)
*A61K 31/513* (2006.01)
(Continued)

(52) U.S. Cl.
CPC ............ *A61K 31/496* (2013.01); *A61K 39/00* (2013.01); *A61P 35/00* (2018.01); *C07K 16/2818* (2013.01); *C07K 16/2827* (2013.01)

(58) Field of Classification Search
CPC .... A61K 31/496; A61K 39/00; A61K 31/513; A61K 39/3955; A61K 45/06;
(Continued)

(56) References Cited

U.S. PATENT DOCUMENTS

2008/0146566 A1 6/2008 Nash et al.
2008/0306058 A1 12/2008 Billich et al.
(Continued)

FOREIGN PATENT DOCUMENTS

CN 107098884 A 8/2017
WO WO 2007/031265 A2 3/2007
(Continued)

OTHER PUBLICATIONS

Wang et al., Interactions between colon cancer cells and tumor-infiltrated macrophages depending on cancer cell-derived colony stimulating factor 1, Oncoimmunol., 5, art. e1122157, pp. 1-12 (Year: 2016).*
(Continued)

*Primary Examiner* — Jeffrey S Lundgren
*Assistant Examiner* — Alexander K. Showalter
(74) *Attorney, Agent, or Firm* — Leydig, Voit & Mayer, Ltd

(57) ABSTRACT

Use of a compound of general formula (A) which is a CFS-IR kinase inhibitor or a pharmaceutically acceptable salt thereof in the preparation of medicaments for treating diseases related to CSF-1R kinase signal transduction pathway or medicaments for regulating immunization. In vivo and in vitro studies show that the compound can signifi-
(Continued)

cantly inhibit CSF-IR kinase activity; significantly inhibits the proliferation of a CSF-1/CSF-1R-driven mouse myeloid leukemia cell line, inhibits the survival of macrophages induced by CSF-1 and reverses M2 polarization phenotype of macrophages, and has an effect superior to that of the marketed medicament Pexidartinib. In a TAM enriched tumor model (MC38 model), the compound significantly antagonizes the tumor immunosuppressive microenvironment and exhibits significant anti-tumor efficacy. The compound has inhibitory effects on tumors that are not sensitive to immune checkpoint drugs, and can enhance the efficacy of immune checkpoint drugs, and has good clinical application prospects.

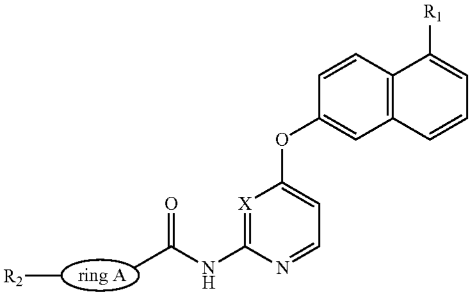

(A)

8 Claims, 5 Drawing Sheets

(51) Int. Cl.

| | |
|---|---|
| ***A61K 39/00*** | (2006.01) |
| ***A61K 39/395*** | (2006.01) |
| ***A61K 45/06*** | (2006.01) |
| ***A61P 29/00*** | (2006.01) |
| ***A61P 35/00*** | (2006.01) |
| ***A61P 35/02*** | (2006.01) |
| ***A61P 37/04*** | (2006.01) |
| ***C07D 401/12*** | (2006.01) |
| ***C07K 16/28*** | (2006.01) |

(58) Field of Classification Search

CPC ...... A61K 2300/00; A61P 35/00; A61P 35/02; A61P 37/04; A61P 29/00; C07K 16/2818; C07K 16/2827; C07D 401/12

See application file for complete search history.

(56) References Cited

U.S. PATENT DOCUMENTS

2010/0113467 A1 5/2010 Manley et al.
2020/0172510 A1 6/2020 Zhang et al.
2025/0171415 A1 * 5/2025 Zhang .................. A61K 31/496

FOREIGN PATENT DOCUMENTS

WO WO 2007/067444 A1 6/2007
WO WO 2008/125691 A2 10/2008
WO WO-2017140269 A1 * 8/2017 ......... A61K 31/4427

OTHER PUBLICATIONS

WO2017140269_Zhang_Machine_Translation (Year: 2017).*

Katoh et al., FGFR inhibitors: Effects on cancer cells, tumor microenvironment and whole-body homeostasis, Int. J. Mol. Med., 38, pp. 3-15 (Year: 2016).*

Inagaki et al., Role of tumor-associated macrophages at the invasive front in human colorectal cancer progression, Cancer Sci., 112, pp. 2557-2932 (Year: 2021).*

Zhang_WO2017140269_MachineTranslation (Year: 2017).*

European Patent Office, Extended European Search Report issued in counterpart European Patent Application No. 21760664.9, mailed on Feb. 27, 2024.

Cannarile et al., "Colony-stimulating factor 1 receptor (CSF1R) inhibitors in cancer therapy", *Journal for Immuno Therapy of Cancer*, 5:53, pp. 1-13 (2017).

Frankel et al., "Cancer Immune Checkpoint Inhibitor Therapy and the Gut Microbiota", *Integrative Cancer Therapies*, 18: 1-10 (2019).

"Immune Checkpoint Inhibitors" Dictionary definition, published Jun. 5, 2015 accessed at URL: https://oncolo.jp/dictionary/immunecheckpintinhibitor.

Katoh, "Fibroblast growth factor receptors as treatment targets in clinical oncology", *Nature Review*, 16: 105-122 (2019).

Kang et al., "A Selective FGFR inhibitor AZD4547 suppresses RANKL/M-CSF/OPG-dependent ostoclastogenesis and breast cancer growth in the metastatic bone microenvironment", *Scientific Reports*, 9(1): 8726, pp. 1-12 (2019).

Peng et al., "Preclinical evaluation of 3D185, a novel potent inhibitor of FGFR1/2/3 and CSF-1R, in FGFR-dependent and macrophage-dominant cancer models", *Journal of Experimental & Clinical Cancer Research*, 38(1): 372, pp. 1-16 (2019).

International Searching Authority, International Search Report and Written Opinion issued in International Patent Application No. PCT/CN2021/078098, mailed on May 26, 2021.

Jiang et al., "SOMCL-085, a novel multi-targeted FGFR inhibitor, displays potent anticancer activity in FGFR-addicted human cancer models", *Acta Pharmacologica Sinica*, vol. 39, pp. 243-250 (2018).

Palakurthi et al., "The Combined Effect of FGFR Inhibition and PD-1 Blockade Promotes Tumor-Intrinsic Induction of Antitumor Immunity", *Cancer Immunology Research*, vol. 7, pp. 1457-1471 (2019).

Wei et al., "Design, synthesis and biological evaluation of a series of novel 2-benzamide-4-(6-oxy-N-methyl-1-naphthamide)-pyridine derivatives as potent fibroblast growth factor receptor (FGFR) inhibitors", *European Journal of Medicinal Chemistry*, vol. 154, pp. 9-28 (2018).

* cited by examiner

USE OF CSF-1R KINASE INHIBITOR

CROSS-REFERENCE TO RELATED APPLICATIONS

The present application is the U.S. National Stage of International Patent Application No. PCT/CN2021/078098, filed Feb. 26, 2021, which claims priority to Chinese Patent Application No. 202010128115.4 filed with the China National Intellectual Property Administration on Feb. 28, 2020, which are each incorporated herein by reference in its entirety.

TECHNICAL FIELD

The present application pertains to the medical field. Specifically, the present application relates to use of a CSF-1R kinase inhibitor in the manufacture of a medicament for the treatment of a disease associated with the CSF-1R kinase signaling pathway or for an improvement of a tumor immunosuppressive status.

BACKGROUND OF THE INVENTION

Tumor microenvironment, which functionally act in its entirety and is inseparable, plays an important role in tumor progression. Numerous stromal cells in the microenvironment, such as tumor-associated macrophages, dendritic cells (DC), regulatory T cells (Treg), fibroblasts, or killer T cells, advance tumor progression by interacting with tumor cells.

Among them, tumor-associated macrophages (TAMs) are a class of important microenvironmental stromal cells. In some tumor tissues, the proportion of macrophages can be up to 50%. Generally, substantial infiltration of TAMs in tumors is considered as an important indicator of poor prognosis of tumor patients. TAMs not only directly inhibit the killing effect of effector T cells and cooperatively facilitate tumor immunosuppressive microenvironment, but also promote tumor cell growth and metastasis by facilitating intratumor angiogenesis. It is generally believed that in TAMs, M1-biased macrophages have a tumor-suppressing effect, whereas M2-biased macrophages have a tumor-promoting effect. Colony stimulating factor 1 receptor (CSF-1R) is expressed in macrophages and is critical to the differentiation of TAMs towards M2 polarization phenotype as well as the maintenance, survival and proliferation of TAMs. Therefore, targeting CSF-1R, inhibiting the M2-biased tumor-promoting phenotype of TAMs, rebuilding an immunosuppressive microenvironment in the body, and effectively activating killer T cells have become important anti-tumor targeting strategies, and have significant potentials in applications to various refractory or high-incidence tumors, such as pancreatic cancer, lung cancer, colon cancer, and breast cancer.

Pexidartinib (PLX3397, trade name: Turalio), the first CSF-1R-targeting drug developed by Daiichi Sankyo Company Limited, was marketed in the United States on Aug. 3, 2019 and was approved for the treatment of tenosynovial giant cell tumor (TGCT), a rare disease, in adult patients. However, Pexidartinib has significant toxic side effects, and a black box warning is attached to the drug label, indicating that the drug has a risk of severe and potentially fatal liver injury. It can be seen that the development of a safe and effective drug targeting CSF-1R for treating high-incidence solid tumors has not been successful. Therefore, further research is necessary to meet clinical needs.

SUMMARY OF THE INVENTION

WO 2017/140269 A1 discloses a compound represented by formula (A), in particular a compound having the structure of formula (I), (A)

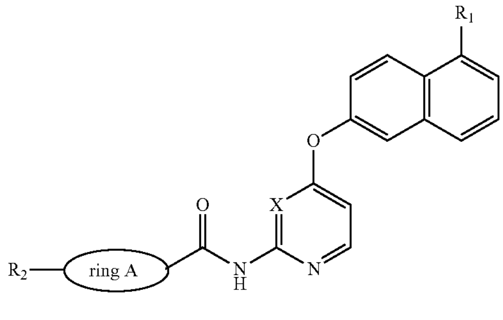

(I)

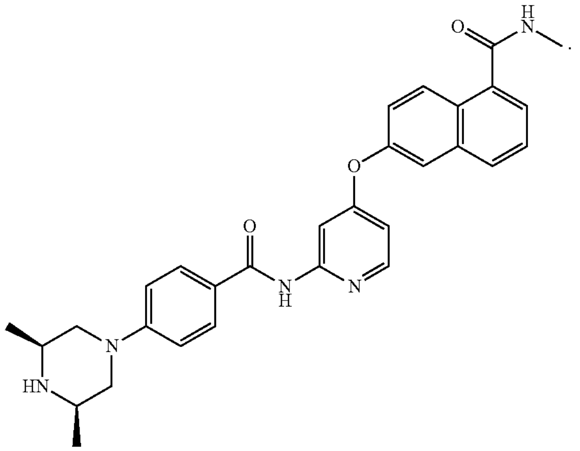

Such compounds are FGFR inhibitors with excellent activities and can directly inhibit tumor cell proliferation. During the research and development process, the inventors of the present application surprisingly found that compound I was also a potent inhibitor of CSF-1R kinase, which could inhibit the M-biased 2 tumor-promoting phenotype of TAMs, activate $CD8^+$ T cells, antagonize the tumor immunosuppressive microenvironment, and enhance the anti-tumor efficacy of immune checkpoint drugs. Compound I showed significant drug efficacy in multiple subcutaneous xenotransplanted tumor models of murine-derived cells and transgenic models.

The most important progress in cancer treatment in the past decade lies in immune checkpoint drugs represented by anti-CTLA-4 antibodies and anti-PD-1/anti-PD-L1 antibodies. Such immunotherapies can repair anti-tumor immunity, thereby reversing immune escape of tumors and promoting tumor cell death. The indications of such immunotherapies have been being expanded, and many of previous standard therapies have been replaced with the therapies. However, it cannot be ignored that the immune system may be over-activated, resulting in an increase of immune-related adverse events. It is reported that up to 60% of patients treated with Yervoy, an anti-CTLA-4 antibody, would experience immune-related adverse events, of which 10-30% were severe (grade 3-4) immune-related adverse events. The adverse events were dose-dependent. Approximately 10% of patients treated with anti-PD-1 antibodies would experience ≥grade 3 immune-related adverse events, including fatigue, headache, arthralgia, rash, pruritus, pneumonia, diarrhea and/or colitis, hepatitis and endocrine diseases. The combination administration of an anti-CTLA-4 antibody with an anti-PD-1 antibody increases the incidence and severity of immune-related adverse events. Some of the patients treated with Bavencio, anti-PD-L1 antibody, experienced an infusion-related response predominantly of grade 1-3 severity. Generally, these adverse effects are dose-related. Lowering the dose can reduce or alleviate adverse effects, while, however, impacting the anti-tumor effect. Therefore, how to enhance the anti-tumor effects of immune checkpoint drugs or strengthening their anti-tumor effects at low doses is an urgent technical problem to be solved.

There is provided in the present application use of a compound represented by formula (A), or a pharmaceutically acceptable salt thereof, in the manufacture of a CSF-1R inhibitor medicament, (A)

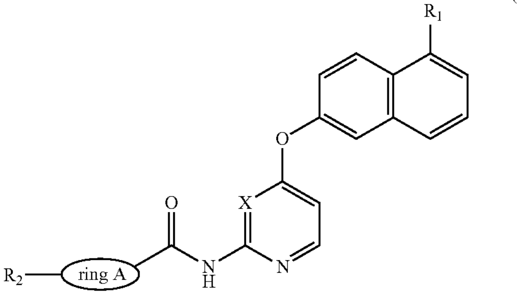

wherein X is selected from the group consisting of CH and N;

ring A can be selected from the group consisting of substituted or unsubstituted 6-10 membered aryl, and substituted or unsubstituted 5-12 membered heteroaryl, wherein said substituted group has one or more hydrogen atoms substituted with a substituent selected from the group consisting of $C_1$-$C_8$ alkyl, $C_1$-$C_8$ alkoxy, $C_1$-$C_8$ alkylamino, halogen, and halo $C_1$-$C_8$ alkyl;

$R_1$ is selected from the group consisting of —$CONHR_3$ and —$COOR_3$;

$R_2$ is selected from the group consisting of substituted or unsubstituted $C_1$-$C_8$ alkyl, substituted or unsubstituted $C_1$-$C_8$ alkoxy, substituted or unsubstituted 4-10 membered heterocyclyl, substituted or unsubstituted amino, substituted or unsubstituted $C_1$-$C_8$ alkylamino, and —$NHCOR_3$; wherein said substituted group has one or more substituents selected from the group consisting of $C_1$-$C_8$ alkyl, hydroxy, hydroxy $C_1$-$C_8$ alkyl, —$COOR_3$, amino-substituted $C_3$-$C_{10}$ cycloalkyl, and 4-10 membered heterocycloalkyl which is unsubstituted or has one or more substituents selected from the group consisting of halogen atoms, hydroxy and $C_1$-$C_8$ alkyl;

$R_3$ is selected from the group consisting of hydrogen, $C_1$-$C_8$ alkyl, and $C_2$-$C_{10}$ alkenyl.

In one embodiment, in the compound represented by formula (A), ring A is selected from the group consisting of substituted or unsubstituted 6-10 membered aryl, and substituted or unsubstituted 5-10 membered heteroaryl.

In one embodiment, in the compound represented by formula (A), ring A is selected from the group consisting of substituted or unsubstituted 6-10 membered aryl, and substituted or unsubstituted 5-6 membered heteroaryl.

In one embodiment, in the compound represented by formula (A), ring A is a substituted or unsubstituted group selected from the group consisting of a benzene ring, a naphthalene ring, a pyridine ring, a pyrazine ring, a thiophene ring, a furan ring, an imidazole ring, a pyrrole ring, an oxazole ring, a thiazole ring, a pyrazole ring, an indole ring, a pyrimidine ring, a benzofuran ring, a benzothiazole ring, a benzimidazole ring, a quinoline ring, and an isoquinoline ring.

In one embodiment, in the compound represented by formula (A), ring A is selected from the group consisting of a substituted or unsubstituted benzene ring, a substituted or unsubstituted thiazole ring, a substituted or unsubstituted oxazole ring, and a substituted or unsubstituted pyrimidine ring.

In one embodiment, in the compound represented by formula (A), $R_2$ is selected from the group consisting of substituted or unsubstituted $C_1$-$C_4$ alkyl, substituted or unsubstituted $C_1$-$C_4$ alkoxy, substituted or unsubstituted 5-6 membered heterocyclyl, substituted or unsubstituted amino, substituted or unsubstituted $C_1$-$C_4$ alkylamino, and —$NHCOR_3$; wherein said substituted group has one or more substituents selected from the group consisting of $C_1$-$C_8$ alkyl, hydroxy, hydroxy $C_1$-$C_8$ alkyl, —$COOR_3$, amino-substituted $C_3$-$C_{10}$ cycloalkyl, and 4-10 membered heterocycloalkyl which is unsubstituted or has one or more substituents selected from the group consisting of halogen atoms, hydroxy or $C_1$-$C_8$ alkyl.

In one embodiment, in the compound represented by formula (A), $R_3$ is selected from hydrogen, $C_1$-$C_6$ alkyl, and $C_2$-$C_6$ alkenyl.

In one embodiment, in the compound represented by formula (A), $R_3$ is selected from hydrogen, $C_1$-$C_4$ alkyl, and $C_2$-$C_4$ alkenyl.

In one embodiment, in the compound represented by formula (A), $R_3$ is selected from hydrogen, methyl, and vinyl.

In one embodiment, the compound represented by formula (A) is preferably a compound represented by the following formula (I) (also referred to as herein compound I):

(I)

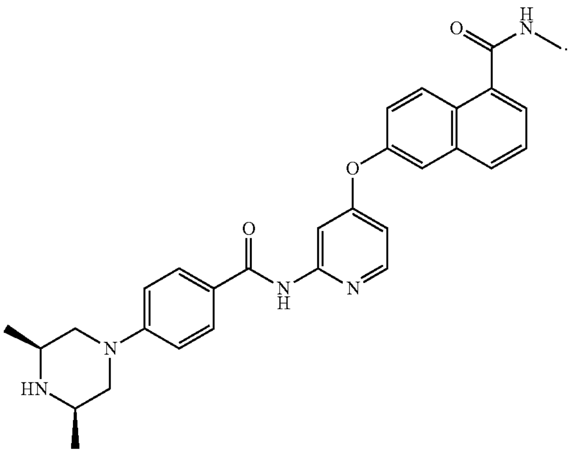

There is provided in the present application use of the compound represented by formula (A) or a pharmaceutically acceptable salt thereof, particularly compound I or a pharmaceutically acceptable salt thereof, in the manufacture of a medicament for the treatment of a disease associated with the CSF-1R kinase signaling pathway.

The disease associated with the CSF-1R kinase signaling pathway in the present application includes a cancer or tumor, hyperplasia, an immune disorder, and an inflammatory disorder, preferably a cancer or tumor. The cancer or tumor in the present application is preferably a CSF-1/CSF-1R-dependent cancer or tumor, or a TAMs-enriched tumor. Preferably, the CSF-1/CSF-1R-dependent cancer or tumor includes CSF-1/CSF-1R-dependent leukemia, and tenosynovial giant cell tumor. Preferably, the TAMs-enriched tumor includes, but not limited to, colon cancer or colorectal cancer.

In another aspect, there is provided in the present application use of the compound represented by formula (A) or a pharmaceutically acceptable salt thereof, particularly compound I, or a pharmaceutically acceptable salt thereof, in the manufacture of a medicament for immunoregulation. The immunoregulation is preferably immunopotentiation. The immunopotentiation may be, for example, an improvement of a tumor immunosuppressive state. The improvement of tumor immunosuppressive state is preferably inhibiting the survival of M2-biased macrophages, reversing an M2-biased polarization phenotype of macrophages and the inhibitory effect of the M2-biased polarization phenotype of macrophages on $CD8^+$ T cells, or rebuilding an immunosuppressive microenvironment in the body.

In another aspect, there is provided in the present application the use of the compound represented by formula (A) or a pharmaceutically acceptable salt thereof, particularly compound I or a pharmaceutically acceptable salt thereof, in the manufacture of a medicament for inhibiting proliferation of macrophages with an M2-biased polarization phenotype.

In another aspect, there is provided in the present application use of the compound represented by formula (A) or a pharmaceutically acceptable salt thereof, particularly compound I or a pharmaceutically acceptable salt thereof, in the manufacture of a medicament for the treatment or inhibition of a tumor. Preferably, the tumor is insensitive to an immune checkpoint drug. The immune checkpoint drug is preferably an anti-PD-1 antibody, or an anti-PD-L1 antibody. The tumor includes, but not limited to, colon cancer, and colorectal cancer.

In another aspect, there is provided in the present application use of the compound represented by formula (A) or a pharmaceutically acceptable salt thereof, particularly compound I or a pharmaceutically acceptable salt thereof, in the manufacture of a medicament for enhancing the anti-tumor efficacy of an immune checkpoint drug, wherein the immune checkpoint drug is preferably an anti-PD-1 antibody, or an anti-PD-L1 antibody.

In another aspect, there is provided in the present application use of the compound represented by formula (A) or a pharmaceutically acceptable salt thereof, particularly compound I or a pharmaceutically acceptable salt thereof, in combination with an immune checkpoint drug in the manufacture of an anti-tumor medicament, wherein the immune checkpoint drug is preferably an anti-PD-1 antibody, or an anti-PD-L1 antibody.

In another aspect, there is provided in the present application use of the compound represented by formula (A) or a pharmaceutically acceptable salt thereof, particularly compound I or a pharmaceutically acceptable salt thereof, in the manufacture of an anti-tumor medicament for use in combination with an immune checkpoint drug, wherein the immune checkpoint drug is preferably an anti-PD-1 antibody, or an anti-PD-L1 antibody.

Further, in the above use, the medicament comprises a therapeutically effective amount of the compound represented by formula (A), or a pharmaceutically acceptable salt thereof, particularly compound I, or a pharmaceutically acceptable salt thereof, and optionally, a pharmaceutically acceptable excipient or carrier.

The administration mode of the medicament of the present application is not particularly limited. Representative administration modes include, but not limited to, oral, intratumoral, rectal, parenteral (intravenous, intramuscular or subcutaneous) and topical administration. Accordingly, the medicament of the present application can be formulated into a variety of clinically acceptable formulations, including formulations for oral administration, injection, topical administration or external application.

Preferably, the compound represented by formula (A) or a pharmaceutically acceptable salt thereof, particularly compound I or a pharmaceutically acceptable salt thereof of the present application can be used clinically alone or in combination with an additional therapeutic agent. The additional therapeutic agent is selected from anti-tumor drugs or immunomodulators. For example, the compound of the present application can be used in combination with an immune checkpoint drug including an anti-PD-1 antibody, or an anti-PD-L1 antibody. For convenience of clinical use, compound I or a pharmaceutically acceptable salt thereof of the present application can be prepared with the additional therapeutic agent into a compound medicament. The additional therapeutic agent is preferably an anti-tumor drug or an immunomodulator, such as an immune checkpoint drug, preferably an anti-PD-1 antibody, or an anti-PD-L1 antibody.

There is further provided in the present application a pharmaceutical composition comprising a compound represented by formula (A) or a pharmaceutically acceptable salt thereof, particularly compound I or a pharmaceutically acceptable salt thereof, and an immune checkpoint drug. The immune checkpoint drug is preferably an anti-PD-1 antibody, or an anti-PD-L1 antibody.

There is further provided in the present application a method of using the medicament comprising the step of administering a therapeutically effective amount of compound I or a pharmaceutically acceptable salt thereof of the present application to a mammal (e.g., a human) in need of treatment.

There is provided in the present application a method of treating a disease associated with the CSF-1R kinase signaling pathway, comprising the step of administering a therapeutically effective amount of the compound represented by formula (A) or a pharmaceutically acceptable salt thereof, particularly compound I or a pharmaceutically acceptable salt thereof, of the present application, to a mammal (such as a human) in need of treatment of said disease. The disease associated with the CSF-1R kinase signaling pathway in the present application includes a cancer or tumor, hyperplasia, an immune disorder, and an inflammatory disorder, preferably a cancer or tumor. The above cancer or tumor is preferably a CSF-1/CSF-1R-dependent cancer or tumor, or a TAMs-enriched tumor. The CSF-1/CSF-1R-dependent cancer or tumor includes CSF-1/CSF-1R-dependent leukemia, and tenosynovial giant cell tumor. The TAMs-enriched tumor includes, but not limited to, colon cancer and colorectal cancer.

There is further provided in the present application a method of regulating immunity, comprising the step of administering a therapeutically effective amount of the compound represented by formula (A) or a pharmaceutically acceptable acceptable salt thereof, particularly compound I or a pharmaceutically acceptable salt thereof, of the present application to a mammal (such as a human) in need of immunoregulation. The immunoregulation is preferably immunopotentiation. The immunopotentiation may be, for example, an improvement of a tumor immunosuppressive state. The improvement of tumor immunosuppressive state is preferably inhibiting the survival of M2-biased macrophages, reversing an M2-biased polarization phenotype of macrophages and the inhibitory effect of the M2-biased polarization phenotype of macrophages on $CD8^+$ T cells, or rebuilding an immunosuppressive microenvironment in the body.

There is further provided in the present application a method of treating or inhibiting a tumor, comprising the step of administering a therapeutically effective amount of the compound represented by formula (A) or a pharmaceutically acceptable salt thereof, particularly compound I or a pharmaceutically acceptable salt thereof of the present application, to a mammal (such as a human) in need of treatment or inhibition of the tumor. Preferably the tumor is insensitive to an immune checkpoint drug. The immune checkpoint drug is preferably an anti-PD-1 antibody, or an anti-PD-L1 antibody. The tumor includes, but not limited to, colon cancer, and colorectal cancer.

There is further provided in the present application a method of enhancing the anti-tumor efficacy of an immune checkpoint drug, comprising the step of administering the compound represented by formula (A) or a pharmaceutically acceptable salt thereof, particularly compound I or a pharmaceutically acceptable salt thereof, of the present application, in combination with the immune checkpoint drug, to a mammal (e.g., a human) in need of treatment or inhibition of the tumor. The immune checkpoint drug is preferably an anti-PD-1 antibody, or an anti-PD-L1 antibody.

There is further provided in the present application a method of treating or inhibiting a tumor, comprising the step of administering a therapeutically effective amount of the compound represented by formula (A) or a pharmaceutically acceptable salt thereof, particularly compound I or a pharmaceutically acceptable salt thereof of the present application, in combination with an immune checkpoint agent to a mammal (e.g., a human) in need of treatment or inhibition of the tumor. The immune checkpoint drug is preferably an anti-PD-1 antibody, or an anti-PD-L1 antibody. The tumor includes, but not limited to, colon cancer, and colorectal cancer.

"A therapeutically effective amount" as used herein refers to a pharmaceutically effective administration dose, i.e., an amount of an active compound (i.e., the compound represented by formula (A) or a pharmaceutically acceptable salt thereof, particularly compound I or a pharmaceutically acceptable salt thereof) sufficient to significantly ameliorate a condition without causing severe side effects. For a person of 60 kg body weight, the compound represented by formula (A) or a pharmaceutically acceptable salt thereof, particularly compound I or a pharmaceutically acceptable salt thereof, is generally administered at a daily dose of 0.01-2000 mg, preferably 0.5-500 mg or 1-500 mg, or 0.5-250 mg, or 0.5-200 mg, or 0.5-150 mg, or 0.5-100 mg, or 0.5-50 mg, or 0.5-40 mg, or 0.5-30 mg, most preferably 0.5-25 mg. Exemplary effective administration doses are, for example, 0.5 mg, 0.75 mg, 0.87 mg, 1 mg, 1.25 mg, 1.5 mg, 1.75 mg, 2 mg, 2.5 mg, 2.75 mg, 3 mg, 3.25 mg, 3.5 mg, 3.75 mg, 4 mg, 4.25 mg, 4.5 mg, 4.75 mg, 5 mg, 5.25 mg, 5.5 mg, 5.75 mg, 6 mg, 6.25 mg, 6.5 mg, 6.75 mg, 7 mg, 7.25 mg, 7.5 mg, 7.75 mg, 7.87 mg, 8 mg, 8.25 mg, 8.5 mg, 8.75 mg, 9 mg, 9.25 mg, 9.5 mg, 9.75 mg, 10 mg, 10.5 mg, 11 mg, 12 mg, 13 mg, 14 mg, 15 mg, 16 mg, 17 mg, 18 mg, 19 mg, 20 mg, 22 mg, or 25 mg. Preferably, the above daily dose is based on the compound represented by formula (A), particularly compound I. It can be administered in a single dose once a day, in multiple doses in a day, or at intervals. The dosage of anti-PD-1 antibody, or anti-PD-L1 antibody depends on the specific type of antibody, the type of cancer, and the stage of cancer. Each administration dose can be 0.5 mg/kg-30 mg/kg, preferably 1-20 mg/kg. For example, for a person of 60 kg body weight, each administration dose can generally be 1 mg-1,800 mg, such as 50 mg-1,200 mg, or 100 mg-900 mg, 150 mg-600 mg or 200 mg-500 mg. Exemplary doses for each administration are, for example, 60 mg, 100 mg, 120 mg, 150 mg, 180 mg, 210 mg, 240 mg, 270 mg, 300 mg, 330 mg, 360 mg, 400 mg, 500 mg, 600 mg, 900 mg, or 1200 mg. The dosing frequency in interval dosing is, for example, once every 3-7 days or once every 1-6 weeks, e.g., once every 3 days, once every 5 days, once a week, once every 10 days, once every 2 weeks, once every 3 weeks, once every 4 weeks, or once every 6 weeks. The specific dosage and frequency of administration should take into account factors such as the route of administration, or the patient's health status, all of which can be determined by a skilled physician according to conventional skills. The mode of administration is not particularly limited, and representative modes of administration include, but not limited to, oral, intratumoral, rectal, parenteral (intravenous, intramuscular or subcutaneous) and topical administration.

There is further provided in the present application the compound represented by formula (A) or a pharmaceutically acceptable salt thereof, particularly compound I or a pharmaceutically acceptable salt thereof, for use as a CSF-1R inhibitor.

There is further provided in the present application the compound represented by formula (A) or a pharmaceutically acceptable salt thereof, particularly compound I or a pharmaceutically acceptable salt thereof, for use in the treatment of a disease associated with the CSF-1R kinase signaling pathway, including a cancer or tumor, hyperplasia, an immune disorder, and an inflammatory disorder, preferably a cancer or tumor. The cancer or tumor of the present application is preferably a CSF-1/CSF-1R-dependent cancer or tumor, or a TAMs-enriched tumor. Preferably, the CSF-1/CSF-1R-dependent cancer or tumor includes CSF-1/CSF-1R-dependent leukemia, and tenosynovial giant cell tumor. Preferably, the TAMs-enriched tumor includes, but not limited to, colon cancer and colorectal cancer.

There is further provided in the present application the compound represented by formula (A) or a pharmaceutically acceptable salt thereof, particularly compound I or a pharmaceutically acceptable salt thereof, for use in immunoregulation. The immunoregulation is preferably immunopotentiation. The immunopotentiation may be, for example, an improvement of a tumor immunosuppressive state. The improvement of tumor immunosuppressive state is preferably inhibiting the survival of M2-biased macrophages, reversing an M2-biased polarization phenotype of macrophages and the inhibitory effect of the M2-biased polarization phenotype of macrophages on $CD8^+$ T cells, or rebuilding an immunosuppressive microenvironment in the body.

There is further provided in the present application the compound represented by formula (A) or a pharmaceutically acceptable salt thereof, particularly compound I or a pharmaceutically acceptable salt thereof, for use in inhibiting proliferation of macrophages with an M2-biased polarization phenotype.

There is further provided in the present application the compound represented by formula (A) or a pharmaceutically acceptable salt thereof, particularly compound I or a pharmaceutically acceptable salt thereof, for use in the treatment or inhibition of a tumor. Preferably, the tumor is insensitive to an immune checkpoint drug. The immune checkpoint drug is preferably an anti-PD-1 antibody, or an anti-PD-L1 antibody. The tumor includes, but not limited to, colon cancer, and colorectal cancer.

There is further provided in the present application a compound of the general formula (A) or a pharmaceutically acceptable salt thereof, particularly compound I or a pharmaceutically acceptable salt thereof, for use in enhancing the anti-tumor efficacy of an immune checkpoint drug, wherein the immune checkpoint drug is preferably an anti-PD-1 antibody or an anti-PD-L1 antibody.

There is further provided in the present application the compound represented by formula (A) or a pharmaceutically acceptable salt thereof, particularly compound I or a pharmaceutically acceptable salt thereof, for use in combination with an immune checkpoint drug for the treatment or inhibition of a tumor in a mammal (e.g., a human). The immune checkpoint drug is preferably an anti-PD-1 antibody, or an anti-PD-L1 antibody.

In another aspect, there is provided in the present application a pharmaceutical composition comprising the compound represented by formula (A) or a pharmaceutically acceptable salt thereof, particularly compound I or a pharmaceutically acceptable salt thereof, and an immune checkpoint drug for use in the treatment or inhibition of a tumor in a mammal (such as a human). The immune checkpoint drug is preferably an anti-PD-1 antibody, or an anti-PD-L1 antibody.

In the context of the present application, a "CSF-1/CSF-1R-dependent cancer or tumor" refers to a cancer or tumor in which CSF-1/CSF-1R is highly expressed or highly activated. The high expression or high activation of CSF-1/CSF-1R refers to that the expression level or activation level of CSF-1/CSF-1R in tissues and/or cells of a cancer or tumor, as measured by a person skilled in the art using conventional detection methods in the art (including but not limited to enzyme-linked immunosorbent assay, immunohistochemistry, flow cytometry, western blotting, tissue chip, and gene detection) is 130% or more, preferably 150% or more, more preferably 175% or more, further more preferably 200% or more, even more preferably 250% or more, and most preferably 300% or more of the normal level. The normal level may be the expression or activation level of CSF-1/CSF-1R in the corresponding tissues and/or cells of the normal population, or may be the expression or activation level of CSF-1/CSF-1R in the peri-cancerous tissues and/or cells of the same patient.

In the context of the present application, a "TAMs-enriched tumor" refers to a tumor with abundant TAM infiltration in its tumor tissue. A person skilled in the art would be able to use conventional detection methods in the art (including but not limited to enzyme-linked immunosorbent assay, immunohistochemistry, flow cytometry, western blotting, tissue chip, and gene detection) to detect surface markers of TAMs or count TAMs. Where the expression levels of surface markers of TAMs in the tumor tissue are different from those of the corresponding surface markers in a peri-cancerous tissue, or the TAM count in the tumor tissue is 130% or more, preferably 150% or more, more preferably 175% or more, further more preferably 200% or more, even more preferably 250% or more, and most preferably 300% or more of that in a peri-cancerous tissue, it can be considered that the TAM infiltration is abundant, and the tumor can be regarded as a TAMs-enriched tumor. Surface markers of TAMs include, but not limited to, general TAM surface markers, surface markers of tumor-promoting macrophages, and surface markers of tumor-suppressing macrophages. The general TAM surface markers include, but not limited to CD14, CD11c, CD68 and/or CD11b, preferably CD68 and/or CD11b. The surface markers of tumor-promoting macrophages include, but not limited to, CSF1R, CSF1, CD115, CD206, PPARG, ARG1, CD163, CD301, Dectin-1, PDL2, Fizz1, CD204, PD-L1, Arginase-I, YM1, MGL2, Osteopontin, MMPs or CCR2 preferably CD206. The surface markers of tumor-suppressing macrophages include, but not limited to IL1a, IL1b, IL6, NOS2, TLR2, TLR4, CD80, CD86, MHC-II, CD38, CD40, CD64, HLA-DR (CD74) or CD169, preferably CD86 and/or MHC-II. A difference in the expression level of a surface marker refers to that, where the surface marker is a general TAM surface marker, the expression level of the surface marker in a tumor tissue is 130% or more, preferably 150% or more, and more preferably 200% or more of the expression level of the corresponding surface marker in a peri-cancerous tissue; and where the surface marker is a surface marker of tumor-promoting macrophages (e.g., CD206), the expression level of the surface marker in a tumor tissue is 130% or more, preferably 150% or more, and more preferably 200% or more of the expression level of the corresponding surface marker in a peri-cancerous tissue. Preferably, where the surface marker further comprises a surface marker of tumor-suppressing macrophages (e.g., CD86 and/or MHC-II), the expression level of the surface marker of the tumor-suppressing macrophages in the tumor tissue is 80% or less, and preferably 50% or less of the expression level of the corresponding surface marker in a peri-cancerous tissue.

In the context of the present application, a "tumor insensitive to an immune checkpoint drug" refers to that when the tumor is treated with the immune checkpoint drug at conventional doses, the tumor inhibition rate is less than 50%. Preferably, the tumor inhibition rate is less than 30%, preferably less than 20%, and more preferably less than 10% when treated with the immune checkpoint drug at a dose around the lower limit of the conventional dosage range. In one embodiment of the present application, the tumor inhibition rate is expressed as the tumor growth inhibition ratio TGI (%), and the calculation formula of TGI (%) is: $TGI\ (\%)=100\times\{1-[(V_{Treated\ Final\ day}-V_{Treated\ Day\ 0})/(V_{Control\ Final\ day}-V_{Control\ Day\ 0})]$, where V is the tumor volume, and is calculated as $V=\frac{1}{2}\times a\times b^2$, where "a" and "b" are the length and width of the tumor, respectively.

In the context of the present application, anti-PD-1 antibodies include, for example, CD279, nivolumab, pembrolizumab, toripalimab, sintilimab, camrelizumab and tislelizumab. Anti-PD-L1 antibodies include, for example, CD274, durvalumab, and atezolizumab.

The values or numeral ranges in the present application may vary within ranges acceptable in the art, e.g., ±10%, or ±9%, or ±8%, or ±7%, or ±6%, or ±5%, or ±4%, or ±3%, or ±2%, or ±1% on the basis of the indicated values or numeral ranges.

In the context of the present application, the compound represented by formula (A) or a pharmaceutically acceptable salt thereof, particularly compound I or a pharmaceutically acceptable salt thereof, is not particularly limited, and preferably include inorganic acid salts, organic acid salts, alkyl sulfonates and aryl sulfonates. Inorganic acid salts include hydrochloride, hydrobromide, nitrate, sulfate, and phosphate. Organic acid salts include formate, acetate, propionate, benzoate, maleate, fumarate, succinate, tartrate, and citrate. Alkyl sulfonates include methanesulfonate, and ethanesulfonate. Aryl sulfonates include benzenesulfonate, and p-toluenesulfonate.

In the context of the present application, the term "heterocyclyl" is a cyclic group having 1, 2, 3, 4 or 5 heteroatoms selected from O, N or S.

As used herein the term "alkyl group" is preferably an aliphatic alkyl group, which may be a linear alkyl group, a branched alkyl group, a spirocycloalkyl group, a bridged cycloalkyl group, an alkenylalkyl group, an alkynylalkyl group, a cycloalkyl group, a cycloalkenyl group, a cycloalkynyl group, an alkoxyalkyl group, an alkoxyacylalkyl group, a cycloalkylalkyl group, including, without limitation, methyl, ethyl, n-propyl, isopropyl, n-butyl, isobutyl, tert-butyl, cyclopropyl, cyclobutyl, cyclopentyl, cyclohexyl, allyl, propargyl, cyclobutenyl and cyclohexenyl. The term "$C_1$-$C_8$" is intended to cover groups having 1, 2, 3, 4, 5, 6, 7 or 8 carbon atoms. For example, "$C_1$-$C_8$ alkyl" refers to an alkyl group having 1, 2, 3, 4, 5, 6, 7 or 8 carbon atoms, and "$C_2$-$C_{10}$ alkenyl" refers to an alkenyl group having 2, 3, 4, 5, 6, 7, 8, 9 or 10 carbon atoms.

As used herein, an alkenyl group is preferably a vinyl group, a propenyl group, a butenyl group, a styryl group, or a phenylpropenyl group.

As used herein, a cycloalkyl group may be a saturated or partially unsaturated monocyclic or polycyclic cyclic hydrocarbon group comprising 3 to 20 carbon atoms, preferably 3 to 12 carbon atoms, and more preferably 3 to 10 carbon atoms. Non-limiting examples of monocyclic cycloalkyl include cyclopropyl, cyclobutyl, cyclopentenyl, cyclohexyl, and cyclooctyl. Polycyclic cycloalkyl groups include cycloalkyl groups of spiro, fused and bridged ring.

A heterocyclyl refers to a saturated or partially saturated monocyclic or polycyclic cyclic group, including 4-10 membered heterocyclyl, and the heterocyclyl is a saturated or unsaturated monocyclic ring, bicyclic ring, spiro ring, fused ring, or bridged ring containing one or more heteroatoms (nitrogen, oxygen, or sulfur). Heterocyclyl groups described herein include, but not limited to, groups selected from the group consisting of morpholine rings, piperidine rings, piperazine rings, N-alkyl or acyl-substituted piperazine rings, homopiperazine rings, N-alkyl or acyl-substituted homopiperazine rings, pyrrole, tetrahydropyrrole, and 7H-purine.

An aryl group refers to a 6-10 membered all-carbon monocyclic or fused polycyclic (i.e., rings that share adjacent pairs of carbon atoms) group having a conjugated pi-electron system, such as phenyl and naphthyl. An aryl ring can be fused with a heterocyclyl, heteroaryl or cycloalkyl ring. Non-limiting examples include benzimidazole, benzothiazole, benzoxazole, benzisoxazole, benzopyrazole, quinoline, benzindole, and benzodihydrofuran.

A heteroaryl group refers to a heteroaromatic system comprising 1 to 4 heteroatoms, and 5 to 14 ring atoms, wherein the heteroatoms include oxygen, sulfur, and nitrogen. A heteroaryl is preferably 5- or 6-membered group, such as furyl, thienyl, pyridyl, pyrrolyl, N-alkylpyrrolyl, pyrimidinyl, pyrazinyl, imidazolyl, or tetrazolyl. A heteroaryl group can be fused to an aryl, heterocyclyl or cycloalkyl ring, wherein the ring to which the parent structure is attached is a heteroaryl ring.

Unless otherwise specified, the structural formulae described herein are intended to include all tautomeric, optically isomeric, and stereoisomeric forms (e.g., enantiomers, diastereomers, geometric isomers or conformational isomers), for example, the R and S configurations containing asymmetric centers, (Z) and (E) double bond isomers, and (Z) and (E) conformational isomers. Therefore, single stereochemical isomers as well as a mixture of tautomers or enantiomers, diastereomers or geometric isomers or conformational isomers or tautomers of the present compounds are within the scope of the present application.

The term "tautomer" means that structural isomers having different energies can exceed low energy barriers and thus interconvert into each other. For example, proton tautomers (i.e., proton shift) include interconversion by proton migration, such as 1H-indazole with 2H-indazole, 1H-benzo[d]imidazole with 3H-benzo[d]imidazole. Valence tautomers include interconversion by some bond-forming electron recombination.

The following effects were observed in In vivo and in vitro studies.

(1) Compound I of the present application could significantly inhibit CSF-1R kinase activity in vitro.

(2) Compound I of the present application could significantly inhibit the proliferation of a CSF-1/CSF-1R-driven mouse myeloid leukemia cell line with efficiency being superior to the marketed drug Pexidartinib, suggesting that compound I or a pharmaceutically acceptable salt thereof can be used for the treatment of CSF-1/CSF-1R-dependent diseases, such as CSF-1/CSF-1R-dependent leukemia and tenosynovial giant cell tumor.

(3) Compound I of the present application could inhibit the survival of macrophages induced by CSF-1 in vitro and reverse M2-biased polarization phenotype of macrophages with efficiencies being superior to the marketed drug Pexidartinib. In the TAMs-enriched tumor model (i.e., MC38 model), compound I significantly reduced M2-biased TAM infiltration, reversed the inhibitory effect of M2-biased macrophages on $CD8^+$ T cells, antagonized the tumor immunosuppressive microenvironment, and demonstrated significant anti-tumor efficacy.

(4) For a CT-26 xenograft model, the tumor inhibition rate of an anti-PD-1 antibody (10 mg/kg, administered orally once every three days) alone was only 6.7%. The tumor inhibition rate of compound I (5 mg/kg, administered orally once a day) alone was 45.8%. When the anti-PD-1 antibody (10 mg/kg, orally administered once every three days) was used in combination with compound I at a dose of 5 mg/kg once a day, the tumor inhibition rate could reach 80.8%, suggesting that compound I not only had an inhibitory effect on a tumor insensitive to immune checkpoint drugs, but also could exhibit significant synergistic efficacy when used in combination with immune checkpoint drugs.

The results show that compound I or a pharmaceutically acceptable salt thereof of the present application can exert an anti-tumor therapeutic effect by rebuilding the tumor microenvironment and improving the tumor immunosuppressive state, can enhance the anti-tumor efficacy of immune checkpoint drugs, and thus has a good prospect in clinical application.

DETAILED DESCRIPTION OF THE INVENTION

Figure 1:
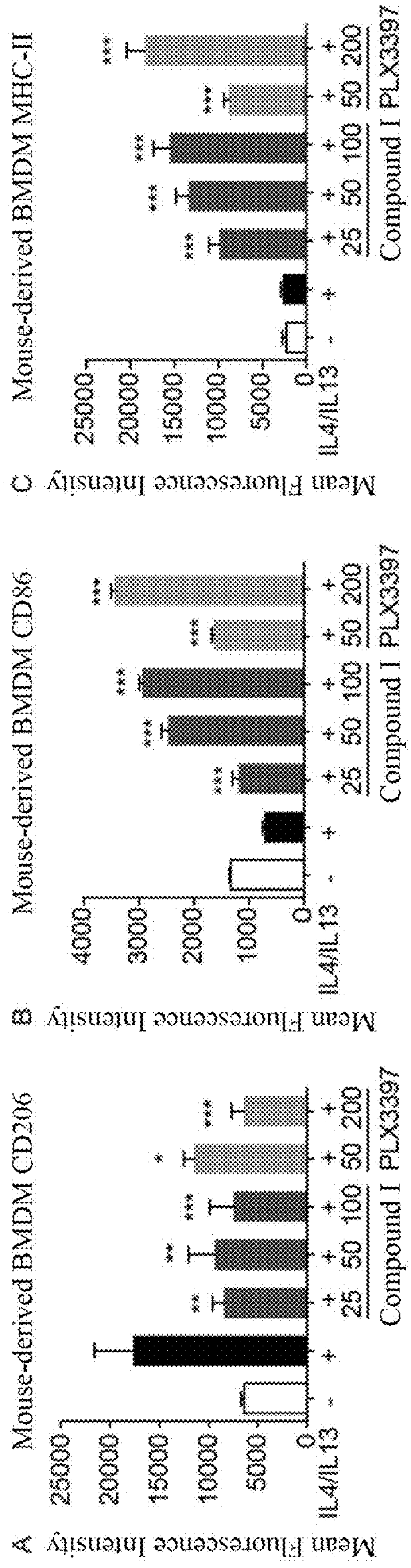
FIG. 1 shows that compound I reverses M2-biased polarization phenotype of murine-derived BMDMs. Panel A shows that compound I downregulates the expression of the surface marker CD206 of M2 macrophages and inhibits M2-biased polarization phenotype of macrophages. Panel B shows that compound I enhances the expression of the surface marker CD86 of M1 macrophages. Panel C shows that compound I enhances the expression of the surface marker MHC-II of M1 macrophages and promotes M1-biased polarization phenotype of macrophages.

The inventions are further illustrated below in reference to particular examples. It should be understood that these examples are merely illustrative of the present application and are not intended to limit the scope of the present application. The experimental methods without specifying their protocols in the following examples are generally carried out according to conventional protocols, or according to protocols recommended by manufacturers. Percentages and parts are by weight unless otherwise stated.

Example 1

Effect of Compound I on CSF-1R Kinase Activity

1. Test Method: Z'-LYTE™ Kinase Assay

The detection was carried out according to the specification of Z'-LYTE™ Kinase Assay kit (PV3190, ThermoFisher), and included the following steps. Z'-LYTE™ Tyrosine 1 Peptide Substrate, Phospho-peptide, 5× Kinase Buffer, ATP, Development Reagent B, Development Buffer, and Stop Reagent were allowed to reach the room temperature and then added sequentially. The effects of compounds at various concentrations on the activity of CSF-1R kinase (PR4598A, ThermoFisher) were tested, and duplicate wells were taken for each concentration. 4% DMSO was used as a co-solvent. After completion of the reaction, 5 μL of Development Reagent B diluted with Development Buffer (1:256) was added to each reaction well. After incubation for 1 h at room temperature, 5 μl of Stop Reagent was added to each reaction well to terminate the reaction. The fluorescence signals were detected by Synergy 2 Microplate Reader (excitation light wavelength: 400 nm, and emission light wavelength: 445 nm or 520 nm).

The inhibition rate for each well was calculated from the fully active well and the control signal well, and the data analysis method was as follows:

$$\%\ \text{phosphorylation} = 1 - \frac{\left(\begin{matrix}\text{fluorescence}\\ \text{intensity ratio}\end{matrix} \times F_{100\%}\right) - C_{100\%}}{(C_{0\%} - C_{100\%}) + \left[\begin{matrix}\text{fluorescence}\\ \text{intensity ratio}\end{matrix} \times (F_{100\%} - F_{0\%})\right]}$$

$$\begin{matrix}\text{inhibition}\\ \text{ratio}\end{matrix} = 1 - \frac{\begin{matrix}\text{phosphorylation}\\ \text{ratio in test well}\end{matrix}}{\begin{matrix}\text{phosphorylation ratio}\\ \text{in control well}\end{matrix}}$$

Fluorescence intensity ratio=ratio of the fluorescence intensity of the "donor" fluorescent molecule coumarin (at 445 nm) to that of the "acceptor" fluorescent molecule fluorescein (at 520 nm) (S445/S520)

$C_{100\%}$=mean fluorescence intensity of "donor" fluorescent molecule coumarin in 100% phosphorylated control wells $C_{0\%}$=mean fluorescence intensity of "donor" fluorescent molecule coumarin in 0% phosphorylated control wells $F_{100\%}$=mean fluorescence intensity of "acceptor" fluorescent molecule fluorescein in 100% phosphorylated control wells $F_{0\%}$=mean fluorescence intensity of "acceptor" fluorescent molecule fluorescein in 0% phosphorylated control well 2. Experimental Results Compound I inhibited CSF-1R kinase with an $IC_{50}$ of 15.0±3.2 nM, which was comparable to the marketed drug Pexidartinib (PLX3397), suggesting that compound I could inhibit the activity of CSF-1R kinase. Therefore, Compound I could act as a CSF-1R kinase inhibitor suggesting that compound I might have an inhibitory effect on CSF-1/CSF-1R-dependent cancers or tumors.

The CSF-1R kinase inhibitor Pexidartinib (PLX3397, trade name: Turalio) was marketed in the United States on Aug. 3, 2019 and was approved for the treatment of a rare disease tenosynovial giant cell tumor (TGCT) in an adult patient. The inhibitory activity of compound I against CSF-1R was comparable to that of Pexidartinib, suggesting that compound I might have an effect of treating tenosynovial giant cell tumor (TGCT).

In addition, CSF-1R kinase is an important target for tumor-associated macrophages. Compound I had a significant inhibitory effect on CSF-1R kinase activity, suggesting that it also has the potential to rebuild the tumor microenvironment and antagonize the tumor.

TABLE 1

Effect of Compound I on CSF-1R Kinase Activity

| Compound | $IC_{50}$(nM) |
|---|---|
| Compound I | 15.0 ± 3.2[a] |
| PLX3397 | 14.3 ± 1.0[b] |

Note:
[a]denoted that the $IC_{50}$ values of compound I were independently measured for three times,
[b]denoted that the $IC_{50}$ values of PLX3397 were independently measured for two times, and the $IC_{50}$ values were expressed as mean ± SD.

Example 2

Effects of Compound I on CSF-1R Mediated Cell Proliferation and Primary Macrophage Survival 1. Test Method 1.1 Effect of Compound I on Proliferation of CSF-1R Highly Activated Mouse Myeloid Leukemia Cell M-NFS-60

CSF-1R highly activated mouse myeloid leukemia cell line M-NFS-60 in logarithmic growth phase were seeded into a 96-well culture plate at appropriate densities (the culture medium for culturing M-NFS-60 cells containing 62 ng/ml of human recombinant macrophage colony stimulating factor (M-CSF)) with 90 μL per well. After overnight incubation, compound I at various concentrations were added and the plate was allowed for incubation for 72 h. A solvent control group (negative control) was set. After 72 h-exposure of the cells to the compounds, 10 μL of CCK-8 reagent was added to each well. The culture plate was placed in an incubator at 37° C. for 2-4 h, and then was read with a full-wavelength microplate reader setting at the wavelength of 450 nm.

1.2 Effect of Compound I on CSF-1-Induced Murine-Derived Macrophage Survival

BALB/c mice (female, 6 weeks old, healthy) were sacrificed. Bone marrow cells were taken from their femurs and tibia, and seeded into a 96-well culture plate at appropriate densities (90 μL per well) after erythrobiasis treatment. 100 ng/ml of CSF-1 factor was added to each well to induce macrophages (Bone marrow-derived macrophages, BMDM), and compounds at various concentrations were added and the plate was allowed for incubation for 7 days. A solvent control group (negative control) was set. After 7 day-exposure of the cells to the compounds, 10 μL of CCK-8 reagent was added to each well. The culture plate was placed in an incubator at 37° C. for 2-4 h, and then was read with a full-wavelength microplate reader setting at the wavelength of 450 nm.

1.3 Effect of Compound I on Survival of CSF-1-Induced Human Macrophages

Cryopreserved human-derived peripheral blood (peripheral blood from healthy donors) mononuclear cells (PBMCs) were taken out of liquid nitrogen for recovery. After recovery, the cells were re-suspended at 50 million/mL with the running buffer and DNAase I was added at a final concentration of 100 μg/mL and the plate was allowed for incubation for 15 min at room temperature. After centrifugation at 300 g for 5 min, the supernatant was discarded. The pellet was re-suspended at 50 million cells/mL with the running buffer, and the suspension was filtered through a 70 μM filter screen into a flow tube. The cells were sorted by using CD14+ monocyte negative selection beads sorting kit from STEMCELL company. According to the manufacture's instructions, the specific experimental procedures were as follows.

After cells were re-suspended at 50 million cells/mL, 50 μL of the cocktail was added to each one mL of samples. The samples were incubated at room temperature for 5 min. The magnetic beads were vortexed for 30 sec, and added to the samples. The samples were incubated for further 5 min. The sample volumes were made up to 2.5 mL. The samples were placed on a magnetic frame (STEMCELL, #18000) for 2.5 min. The supernatants were moved into centrifuge tubes, and the tubes were centrifuged at 300 g for 5 min. The cells were re-suspended with 1640 medium to an appropriate volume. 100 ng/ml of CSF-1 factor was added to the cell suspension according to different experimental requirements. The cells were seeded in a 96-well plate at a desired density, and 90 μL of the cell suspension was added to each well. After the cell state was stable, compounds at various concentrations were added and the plate was allowed for incubation for 7 days. A blank solvent control group was set. After the reaction was completed, 10 μL of CCK-8 reagent was added to each well of the 96-well plate. The plate was placed in an incubator at 37° C. for 2-4 h, and then was read with an adjustable wavelength microplate reader setting at a wavelength of 450 nm.

2. Experimental Results

Compound I inhibited CSF-1-mediated proliferation of M-NFS-60 cells in a dose-dependent manner with an $IC_{50}$ of 1.2±0.5 nM.

Compound I inhibited CSF-1-induced macrophage survival in a dose-dependent manner with an $IC_{50}$ of 10.2±0.8 nM for survival inhibition of murine-derived macrophages and 30.5±5.1 nM for survival inhibition of human-derived macrophages.

Notably, although the inhibitory effect of compound I of the present application on CSF-1R kinase activity is comparable to that of the marketed drug Pexidartinib (PLX3397), compound I showed a more potent inhibitory effect on CSF-1R highly activated leukemia cell M-NFS-60 and CSF-1-induced macrophage survival in cellular assays, with its $IC_{50}$ only being about ⅕-1⁄50 of that of PLX3397. This is far beyond the expectations of a person skilled in the art, suggesting that compound I showed better cellular activity and may achieve better therapeutic effect than Pexidartinib (PLX3397) in clinical use.

TABLE 2

$IC_{50}$ of Compound I in Inhibiting Cell Proliferation and Survival of Cells

| Cells | $IC_{50}$ (nM) | |
|---|---|---|
| | Compound I | PLX3397 |
| M-NFS-60 | 1.2 ± 0.5 | 62.6 ± 15.8 |
| BMDM (CSF-1) | 10.2 ± 0.8 | 48.9 ± 5.9 |
| PBMC (CSF-1) | 30.5 ± 5.1 | 237.0 ± 14.7 |

Note:
Compound I and PLX3397 were exposed tp M-NFS-60 cells for 3 days, respectively.
The $IC_{50}$ values for inhibition of cell proliferation were independently measured for three times, and were expressed as mean ± SD.
Compound I and PLX3397 were exposed to BMDM and PBMC cells for 7 days, respectively.
The $IC_{50}$ values for inhibition of cell survival were independently measured for two times, and were expressed as mean ± SD.

Example 3

Compound I Reverses M2-biased Polarization Phenotype of Macrophages

1. Test Methods

BALB/c mice (female, 6 weeks old, healthy) were sacrificed. Bone marrow cells were taken from their femurs and tibia, and seeded into a 6-well culture plate at appropriate densities (2 μL per well) after erythrobiasis treatment. 100 ng/ml of CSF-1 factor was added to each well to induce macrophages (Bone marrow-derived macrophages, BMDM). After 7 days of induction, the cell culture medium was changed. CSF-1 factor was added at the same concentration as above, and M2 polarization of macrophages was induced with 10 ng/ml of IL4 and 10 ng/ml of IL13. While inducing polarization, compounds at various concentrations were added into test wells and negative control wells. After 48 h, the cells were harvested for flow cytometric analysis.

Cells in good condition were collected, and first washed twice with PBS. After washing, each sample was re-suspended with 100 μL of PBS and 0.5 μL of the fluorescent antibody prepared according to the manufacturer's instructions to distinguish dead and live cells was added. The samples were stained in the dark at 4° C. for 30 min. After 30 min, the samples were washed twice with 1 mL of the running buffer and the tubes were centrifuged at 300 g for 5 min at 4° C. The blocking antibody diluent was prepared by adding 2 μL of blocking antibody TruStain fcX™ (anti-mouse CD16/32) per 100 μL running buffer and was added on the basis of the 100 μL system of each sample. After blocking for 10 min, according to the manufacturer's instructions, the fluorescent antibody corresponding to the surface protein was added to the samples, and the reactant was allowed for incubation at 4° C. for 30 min. At this step, a single staining control and an FMO control were set. Then, the samples were washed twice with 1 mL of the running buffer, and centrifuged at 300 g for 5 min at 4° C. each time.

If only surface proteins were to be examined, after centrifugation, the samples were re-suspended with 300 μL of PBS and immediately input into machines, or the samples were fixed with 4% paraformaldehyde for 15 min, and centrifuged at 500 g for 7 min. The supernatants were discarded and the pellets were re-suspended with PBS and stored for further machine analysis.

If intracellular factors were to be examined as well, when the supernatants were discarded after centrifugation, 100 μL of re-suspended samples were retained. IC fixation solution in Intracellular Fixation & Permeabilization Buffer Set was added to each sample based on the 100 μL volume. The samples were placed at 4° C. for fixation for 30 min. After the fixation was completed, the samples were centrifuged at 500 g for 7 min. 10×Permeabilization Buffer was prepared into 1×membrane destructive solution with triple distilled water. After centrifugation, 2 mL of 1×membrane destructive solution was added to each sample to re-suspend the samples, and the samples were centrifuged at 500 g for 7 min. The process was repeated twice. 1×membrane destructive solution was used to prepare the intracellular fluorescent antibody as recommended in the instructions for antibody. The cells were re-suspended in a system of 100 μL per well, and placed at 4° C. to stain for 30 min. At this step, a single staining control and an FMO control were set. Then, the samples were centrifuged at 500 g for 7 min, and washed twice with 2 mL of 1×membrane destructive solution. Finally, the samples were re-suspended with 300 μL of PBS, and stored for further machine analysis.

2. Experimental Results

The experimental results showed that compound I at doses of 25, 50, and 100 nM could significantly inhibit the expression level of the surface marker CD206 (a representative M2-type marker for macrophages) in the mouse-derived BMDM experimental systems (Panel A in FIG. 1). In addition, compound I could significantly enhance the expression levels of the surface markers CD86 and MHC-II (representative M1-type markers for macrophages) (Panels B and C in FIG. 1), suggesting that compound I could reverse the M2-like polarization of macrophages induced by IL4 and IL13, down-regulate the proportion of M2-biased macrophages, and up-regulate the infiltration of M1 macrophages.

Example 4

Compound I Reverses the Inhibitory Effect of Macrophages on $CD8^+$ T Cells

1. Test Methods

Intact spleens were isolated from BALB/c mice (female, 6 weeks old, healthy). The spleens were homogenized in the running buffer, and the homogenate was centrifuged at 300 g for 5 min. Then, the cells were placed into an erythrocyte lysing agent to lyse. The resultant spleen cells were washed twice with PBS, and centrifuged at 300 g for 5 min each time. Then, the cells were re-suspended to 20 million/mL, and CFSE was added at a final concentration of 5 mM. After staining for 15 min, 9 times volume of PBS was added. The mixture was centrifuged at 400 g for 5 min, and washed once with 10 mL of normal culture medium. αCD3/αCD28 and IL-2 were added to the finally obtained spleen cells for stimulation. The cells without added factors were used as a negative control. The cells with added factors were used as a positive control. The other cells were co-cultured with CSF-1-induced BMDMs (100,000/well) pre-treated with compounds and a solvent control. The pre-treated BMDMs were co-cultured with raw spleen cells at a ratio of 1:30. αCD3/αCD28/IL2 was added to activate T cells and the co-culture took for 72 h. After 72 h, eBioscience™ Cell Stimulation Cocktail (plus protein transport inhibitors) (500×) was added to the mixture at a ratio of 1:500, and after incubation for 4 h, spleen cells were harvested and analyzed by flow cytometry for the proliferation of $CD8^+$ T cell subsets and the proportion of activated $CD8^+$ T cells ($IFN\gamma^+$ $CD8^+$ T, $GranzymeB^+CD8^+T$).

2. Experimental Results

Figure 2:
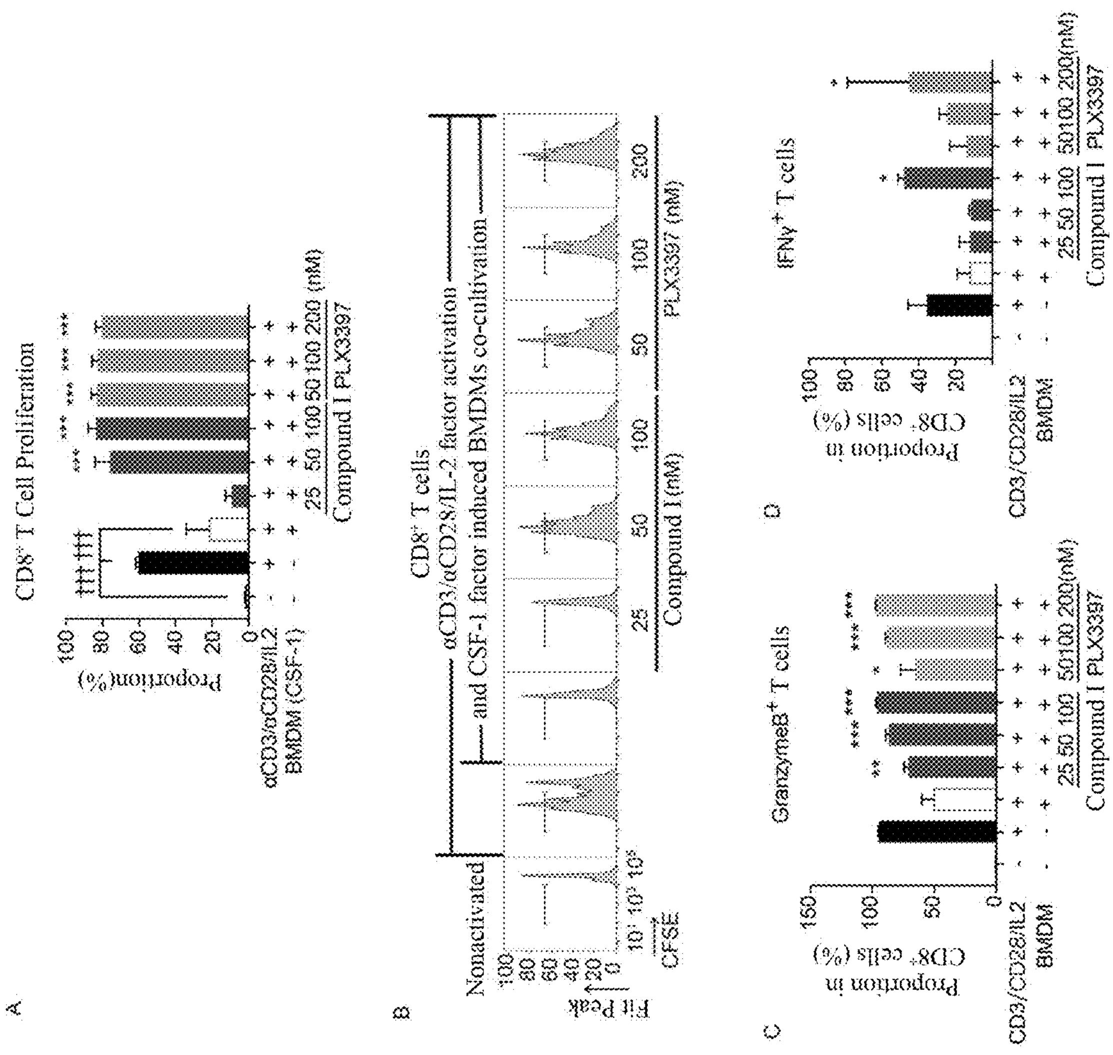
FIG. 2 shows that compound I reverses the inhibitory effect of CSF-1-induced BMDMs on $CD8^+$ T cell proliferation, and reverses the inhibitory effect of CSF-1-induced BMDMs on $CD8^+$ T cell activation. Panel A shows that compound I eliminates the proliferation inhibitory effect of CSF-1-induced BMDMs on $CD8^+$ T cell proliferation. Panel B shows a schematic of the results of representative flow cytometry. Panel C shows that compound I eliminates the inhibitory effect of CSF-1-induced BMDMs on the expression of Granzyme B in $CD8^+$ T cells. Panel D shows that compound I eliminates the inhibitory effect of CSF-1-induced BMDMs on IFNγ expression in $CD8^+$ T cells.

The results showed that addition of αCD3/αCD28/IL2 could activate the proliferation of $CD8^+$ T cells, which was significantly inhibited by addition of CSF-1-induced BMDMs. After pre-incubation of the CSF-1-induced BMDMs with Compound I, the above proliferation inhibitory effect was eliminated (Panels A and B of FIG. 2) and $CD8^+$ T cell proliferation was substantially increased compared to the solvent control group.

Activated $CD8^+$ T cells highly expressed IFNγ and Granzyme B. The detection results of the proportions of $IFN\gamma^+$ $CD8^+$ T and Granzyme $B^+$ $CD8^+$ T cells showed that the ratio of Granzyme B and IFNγ-positive $CD8^+$ T cells was significantly increased in the co-culture system of BMDMs pretreated with compound I and $CD8^+$ T cells compared to the solvent control group (Panels C and D of FIG. 2), indicating that compound I eliminated the immunosuppressive effect of CSF-1-induced BMDMs on activated $CD8^+$ T cells.

Example 5

Effect of Compound I on Immune Microenvironment in Colorectal Cancer MC38 Xenograft Model 1. Test Methods MC38 cells in good condition were re-suspended to 25 million cells/mL. 200 μL of cell suspension was inoculated subcutaneously in the right armpit of each mouse. When the tumor cells formed subcutaneous xenograft in the mice and grew to an average volume of approximately 100 $mm^3$, the mice were randomly assigned to the dosing group and the control group. The test compounds were prepared at the desired concentrations and corresponding equal amount of solvent was used as a solvent control. The drugs were administrated orally, and administrated once per day for 24 consecutive days.

(1) Scanning Experiment of Immune Cell Subpopulation in Tumor Tissue

During the dosing period, the xenograft volumes of the mice and the weights of the mice were measured every 2-4 days. When the MC38 subcutaneous xenograft from the solvent control group of grew to 700-800 $mm^3$, the experiment was stopped. Fresh tumors removed from the mice were sheared with scissors into fragments no more than 2 $mm^3$. The digestive enzyme was prepared according to the instructions of Tumor Dissociation Kit. The tumor tissue mass was re-suspended with 2.5 mL of prepared enzyme solution, and was placed into a gentleMACS™ Dissociator instrument for dissociating the tumor with a selected program. After completion of dissociation, the suspension was filtered with a 70 μM filter screen to obtain a cell suspension. The cell suspension was lysed with an erythrocyte lysing agent for 10 min, centrifuged at 300 g for 5 min, and re-suspended with PBS. Desired amount of cells were taken out after cell counting. The cells were first washed twice with PBS. After washing, each sample was re-suspended with 100 μL of PBS and 0.5 μL of the fluorescent antibody prepared according to the manufacturer's instructions to distinguish dead and live cells was added. The samples were stained in the dark at 4° C. for 30 min. After 30 min, the samples were washed twice with 1 mL of the running buffer and the tubes were centrifuged at 300 g for 5 min at 4° C. The blocking antibody diluent was prepared by adding 2 μL of blocking antibody TruStain fcX™ (anti-mouse CD16/32) per 100 μL running buffer and was added on the basis of the 100 μL system of each sample. After blocking for 10 min, according to the manufacturer's instructions, the fluorescent antibody corresponding to the surface protein was added to the samples, and the reactant was allowed for incubation at 4° C. for 30 min. At this step, a single staining control and an FMO control were set. Then, the samples were washed twice with 1 mL of the running buffer, and centrifuged at 300 g for 5 min at 4° C. each time.

If only surface proteins were to be examined, after centrifugation, the samples were re-suspended with 300 μL of PBS and immediately input into machines, or the samples were fixed with 4% paraformaldehyde for 15 min, and centrifuged at 500 g for 7 min. The supernatants were discarded and the pellets were re-suspended with PBS and stored for further machine analysis.

If intracellular factors were to be examined as well, when the supernatants were discarded after centrifugation, 100 μL of re-suspended samples were retained. IC fixation solution in Intracellular Fixation & Permeabilization Buffer Set was added to each sample based on the 100 μL volume. The samples were placed at 4° C. for fixation for 30 min. After the fixation was completed, the samples were centrifuged at 500 g for 7 min. 10×Permeabilization Buffer was prepared into 1×membrane destructive solution with triple distilled water. After centrifugation, 2 mL of 1×membrane destructive solution was added to each sample to re-suspend the samples, and the samples were centrifuged at 500 g for 7 min. The process was repeated twice. 1×membrane destructive solution was used to prepare the intracellular fluorescent antibody as recommended in the instructions for antibody. The cells were re-suspended in a system of 100 μL per well, and placed at 4° C. to stain for 30 min. At this step, a single staining control and an FMO control were set. Then, the samples were centrifuged at 500 g for 7 min, and washed twice with 2 mL of 1×membrane destructive solution. Finally, the samples were re-suspended with 300 μL of PBS, and stored for further machine analysis.

If nucleoproteins were to be stained at the same time, after centrifugation, each sample is fixed with 200 μL of fixing solution in Foxp3/Transcription Factor Staining Buffer Set for 30 min at 4° C. After the fixation was completed, the samples were centrifuged at 500 g for 7 min. 10×Permeabilization Buffer was prepared into 1×membrane destructive solution with triple distilled water. After centrifugation, 2 mL of 1×membrane destructive solution was added to each sample to re-suspend the samples, and the re-suspended samples were centrifuged at 500 g for 7 min. The process was repeated twice. 1×membrane destructive solution was used to prepare the intracellular fluorescent antibody as recommended in the instructions for antibody. The cells were re-suspended in a system of 100 μL per well, and placed at 4° C. to stain for 30 min. At this step, a single staining control and an FMO control were set. Then, the samples were centrifuged at 500 g for 7 min, and washed twice with 2 mL of 1×membrane destructive solution. Finally, the samples were re-suspended with 300 μL of PBS, and stored for further machine analysis.

(2) Pharmacodynamic Experiments:

During the dosing period, the xenograft volumes of the mice and the weights of the mice were measured every 2-4 days. The experiment was terminated 24 days after dosing.

The tumor volume (TV) was calculated as $TV=\frac{1}{2}\times a\times b^2$, where "a" and "b" are the length and width of an xenograft, respectively.

The evaluation index of the anti-tumor activity was tumor growth inhibition ratio TGI (%), which was calculated as $TGI\ (\%)=100\times\{1-[(V_{Treated\ Final\ day}-V_{Treated\ Day\ 0})/(V_{Control\ Final\ day}-V_{Control\ Day\ 0})]$. Statistical tests were performed using the t test, with $p<0.05$ representing a significant difference.

2. Experimental Results

The inventors selected the MC38 mouse subcutaneous xenograft model with abundant macrophage infiltration in colorectal cancer models to investigate the effect of compound I on the tumor immune microenvironment. Studies had shown that cytotoxic $CD8^+$ T cells were important effectors in immune cells. The infiltration and killing ability of cytotoxic T cells in tumors were a key factor in anti-tumor effects. Activated T cells could exert anti-tumor effects by secreting IFNγ and Granzyme B. M2-biased TAMs would inhibit the proliferation of cytotoxic $CD8^+$ T cells, resulting in a tumor immunosuppressive state. In tumor growth, regulatory T cells (Treg) interacted with a variety of immune cells to produce inhibitory cytokines, promote immunosuppressive tumor microenvironments, promote tumor growth, and impede tumor response to therapy. In view of the important role of macrophages in the MC38 mouse xenograft model, the macrophages infiltration as well as the infiltration and activation of T cells in the M2-biased polarization and lymphocytes were examined by the inventors.

Figure 3:
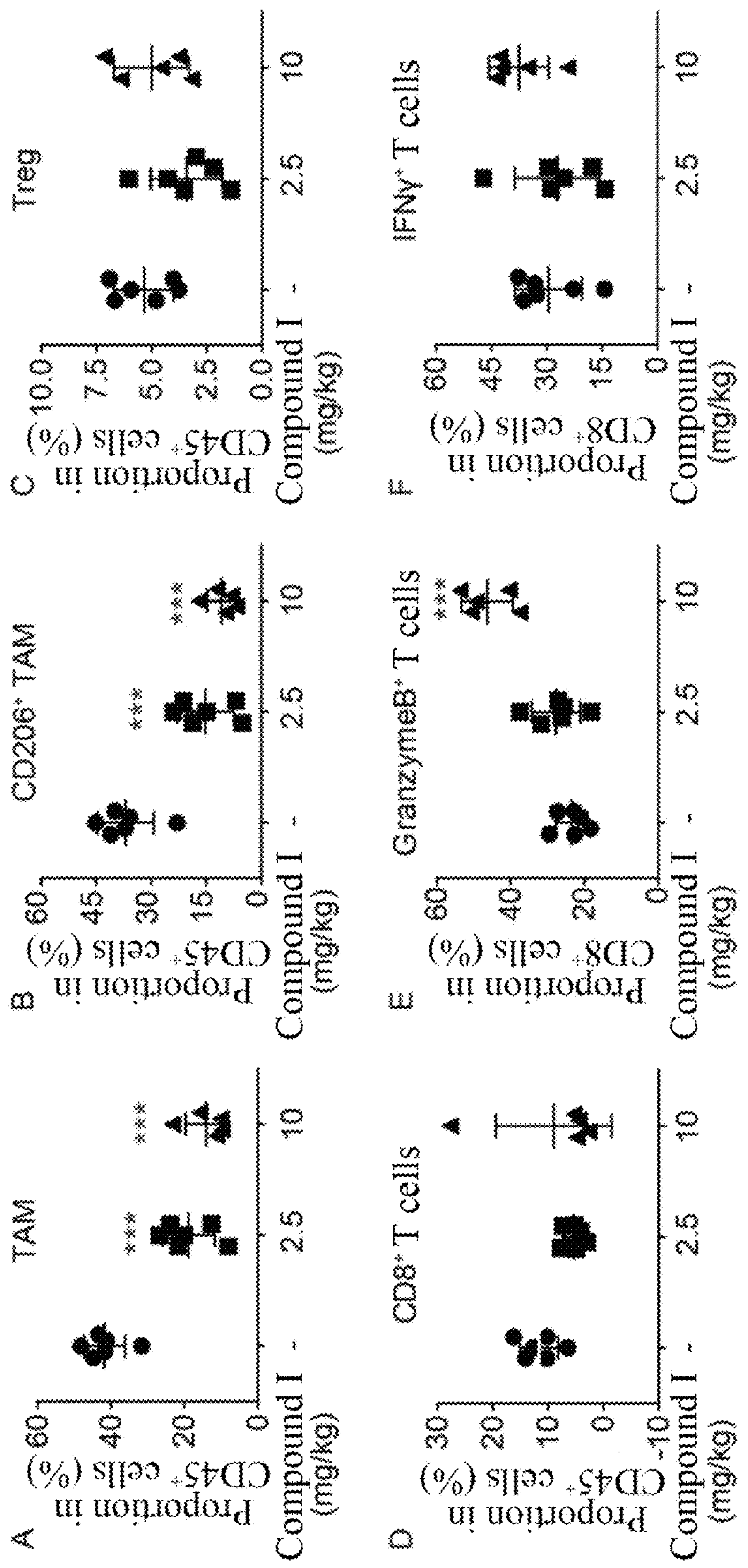
FIG. 3 shows that compound I remodels immune cell infiltration in colon cancer MC38 mouse xenograft model. Panel A shows that compound I significantly inhibits TAM infiltration. Panel B shows that compound I downregulates the proportion of CD206+ macrophages in TAMs. Panel C shows that compound I inhibits Treg cell infiltration. Panel D shows the effect of compound I on $CD8^+$ T cell infiltration. Panel E shows that compound I enhances Granzyme B+T cell infiltration in $CD8^+$ T cells. Panel F shows the effect of compound I on IFNγ+$CD8^+$ T cell infiltration.

The results showed that, compared to the solvent control group, the infiltration of TAMs in the tumor tissue bulk was significantly reduced in each dose group of compound I, and the infiltration of $CD206^+$ M2-biased macrophages in TAMs was further down-regulated (Panels A and B in FIG. 3). The infiltration of Treg cells was significantly reduced under the effect of compound I (Panel C in FIG. 3). The inventors further analyzed the infiltration of $CD8^+$ T cells in T cells and found that, compared to the solvent control group, there was no significant change in the infiltration of $CD8^+$ T cells and IFNγ $CD8^+$ T cells, but the infiltration of Granzyme $B^+CD8^+$ T cells was significantly increased (10 mg/kg group) (Panels D, E and F in FIG. 3).

Figure 4:
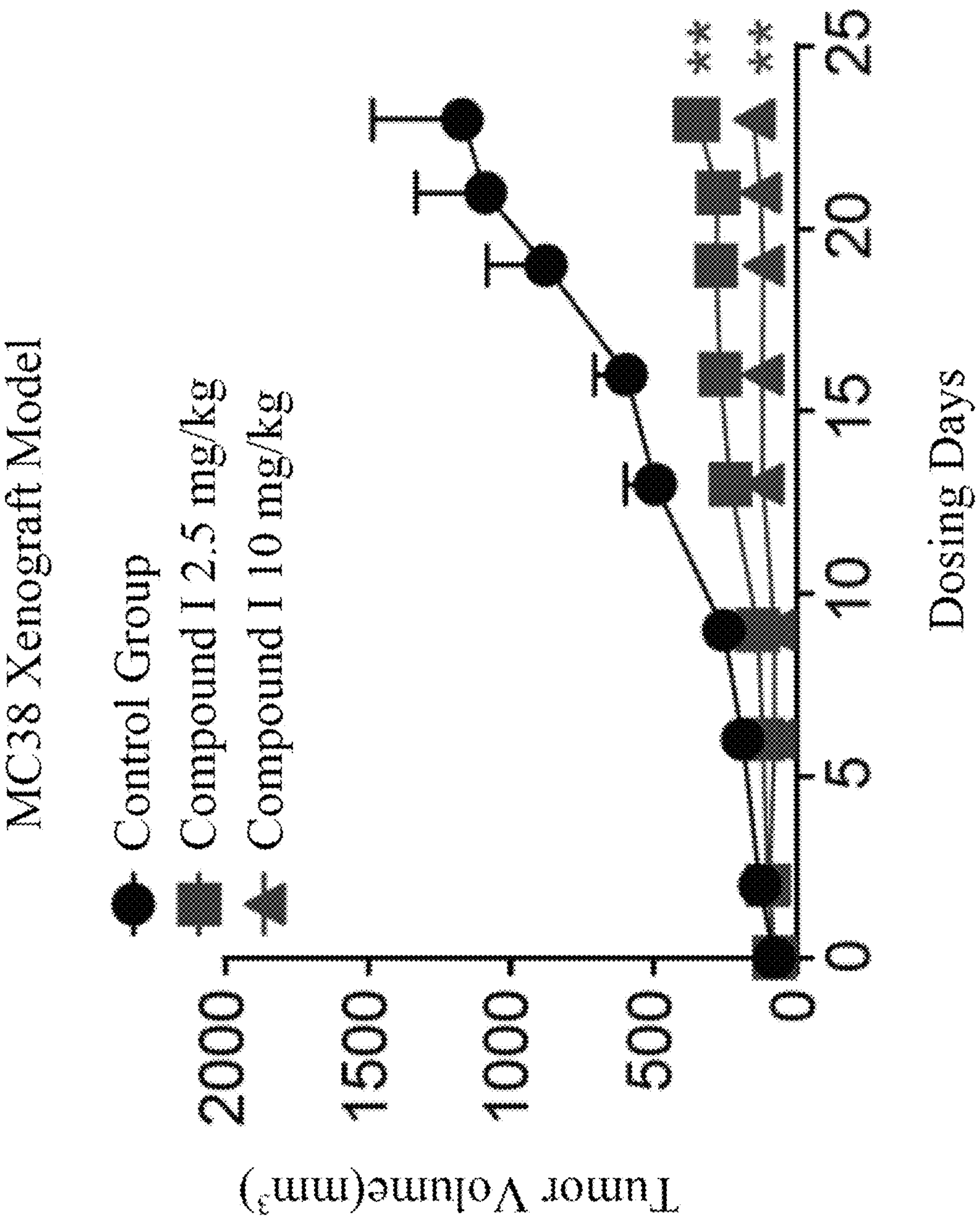
FIG. 4 shows the growth inhibitory effect of compound I on subcutaneous xenografts MC38 in mice.

The results from further anti-tumor activity in vivo assessments suggested that compound I significantly inhibited the growth of murine colon cancer MC38 cell xenografts by targeting CSF-1R, inhibiting the infiltration of macrophages in vivo (particularly M2 macrophages), down-regulating the infiltration of Treg, enhancing the infiltration of activated $CD8^+$ T cells (particularly Granzyme B+$CD8^+$ T cells), rebuilding the entire tumor microenvironment, reversing the tumor immunosuppressive state, and antagonizing the tumor (Table 3, FIG. 4).

Statistical tests were performed using the t test, with p≤0.05 representing a significant difference.

2. Experimental Results

Figure 5:
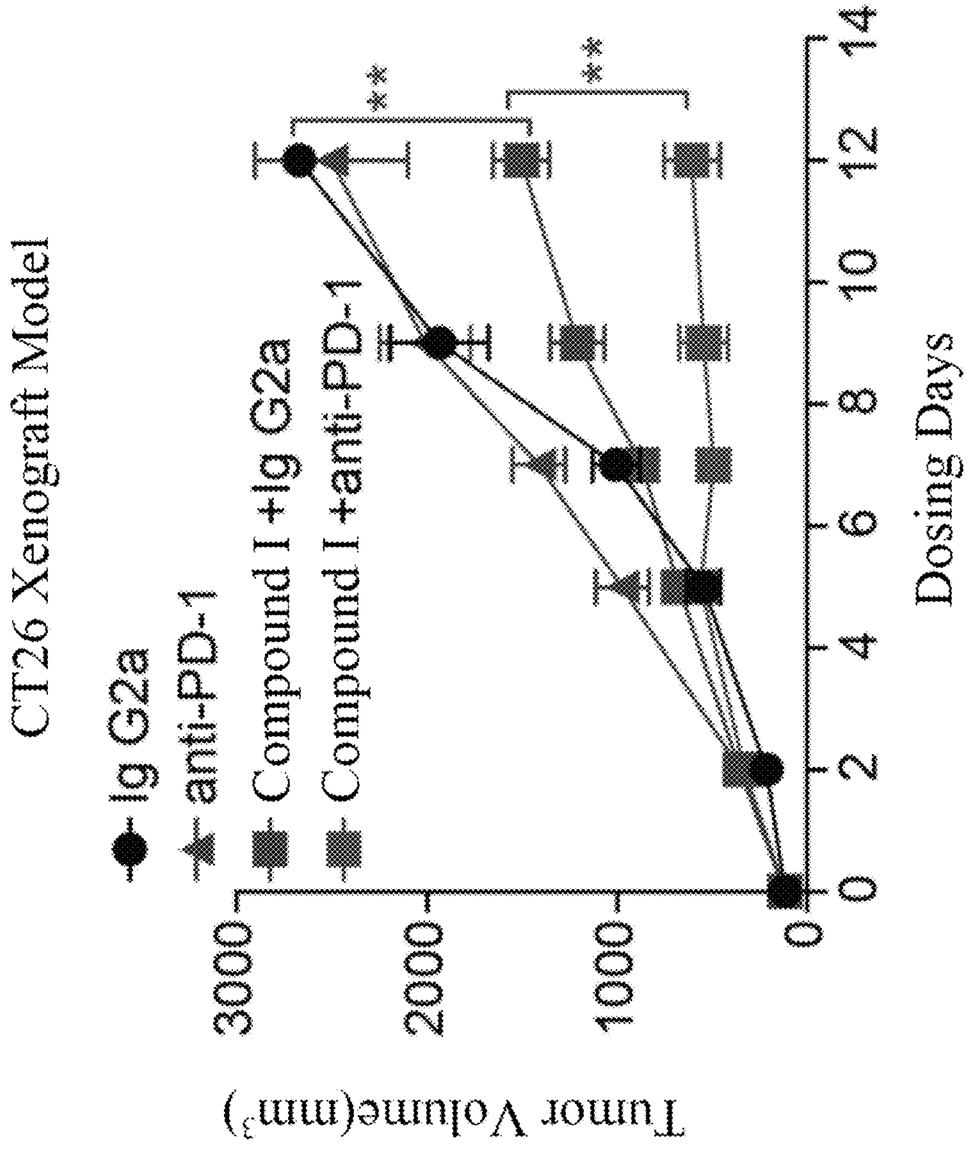
FIG. 5 shows that compound I enhances the inhibitory effect of an anti-PD-1 antibody on the growth of subcutaneous CT-26 xenografts in mice.

The results of this experiment showed that the tumor inhibition rate was only 6.7% with anti-PD-1 antibody alone (10 mg/kg, administered orally once every three days), and the tumor inhibition rate of 5 mg/kg of compound I alone was 45.8%. Where the anti-PD-1 antibody (orally administered once every three days, each dose of 10 mg/kg) was administered in combination with compound I at a dose of 5 mg/kg once a day, the tumor inhibition rate could reach 80.8% (Table 4 and FIG. 5), suggesting that compound I enhanced the anti-tumor effect of the anti-PD-1 antibody in the CT-26 model.

TABLE 3

Inhibitory Ratio of Compound I on Tumor Volume Increase of Mouse Colon Cancer MC38 Xenografts

| | TV (mm3, mean ± SEM) | | | | | TGI (%) | | | | |
|---|---|---|---|---|---|---|---|---|---|---|
| Group | $D_0$ | $D_7$ | $D_{14}$ | $D_{20}$ | $D_{24}$ | $D_0$ | $D_7$ | $D_{14}$ | $D_{20}$ | $D_{24}$ |
| Solvent control | 80 ± 11 | 189 ± 44 | 495 ± 103 | 877 ± 205 | 1,171 ± 315 | / | / | / | / | / |
| Compound I (2.5 mg/kg) | 79 ± 13 | 119 ± 17 | 232 ± 39 | 281 ± 59 | 348 ± 80 | / | 63.3 | 63.0 | 74.6 | 75.3 |
| Compound I (10 mg/kg) | 79 ± 12 | 78 ± 15 | 120 ± 42 | 117 ± 46 | 150 ± 64 | / | 100.9 | 90.1 | 95.2 | 93.4 |

Example 6

Anti-Tumor Efficacy of Immune Checkpoint Drugs Sensitized by Compound I

1. Test Methods

CT-26 cells were subcutaneously inoculated into the right axillary fossa of BALB/c mice at a cell number of $5\times10^6$ per mouse. When the tumor cells successfully formed subcutaneous xenografts in the mice which further grew to an average volume of approximately 100 $mm^3$, the mice were randomly assigned to the dosing group and the control group. For the anti-PD-1 antibody group, an anti-PD-1 antibody (Bio X Cell Company, InVivoMAb anti-mouse PD-1 (CD279) (catalog: BE0273)) was administered orally once every three days at 10 mg/kg for 12 days. The control group was administrated the same amount of Hamster Ig (Rat IgG2a), as the isotype control of the anti-PD-1 antibody, and the administration route, dosage and frequency were same as those for the anti-PD-1 antibody group. For the compound I group (compound I+Rat IgG2a), compound I was administered orally once a day at 5 mg/kg for 12 consecutive days, and Rat IgG2a was administered simultaneously with same mode of administration as the control group. A combination administration group of the anti-PD-1 antibody (10 mg/kg, administered orally once every three days) and compound I (5 mg/kg, administered orally once a day) was set. Throughout the experiment, the tumor volume and the mice's body weights were measured twice a week.

The tumor volume (TV) was calculated as $TV=\frac{1}{2}\times a\times b^2$, where "a" and "b" are the length and width of the xenograft, respectively.

The relative tumor volume (RTV) was calculated from the results of the measurement according to the following equation:

$RTV=V_t/V_0$, where $V_0$ was the tumor volume measured at the beginning of administration (i.e., d0) and Vt was the tumor volume measured at each point.

The evaluation index of the anti-tumor activity was tumor growth inhibition ratio TGI (%), which was calculated as:

$$TGI\ (\%)=100\times\{1-[(V_{Treated\ Final\ day}-V_{Treated\ Day\ 0})/(V_{Control\ Final\ day}-V_{Control\ Day\ 0})]\}.$$

TABLE 4

Tumor Volume Growth Inhibition Rate of Compound I on Mouse Colon Cancer CT26 Xenograft

| Group | TGI (%) |
|---|---|
| Anti-PD-1 antibody | 6.7 |
| Compound I + Rat IgG2a | 45.8 |
| Compound I + anti-PD-1 antibody | 80.8 |

The English abbreviations used in this application and their full terms are as follows.

CSF-1R: Receptor tyrosine kinase colony-stimulating factor 1 receptor

CSF-1: Receptor tyrosine kinase colony-stimulating factor 1

TAM: Tumor-associated macrophage

Treg: Regulatory T cells

DC: Dendritic cells

PBMC: Peripheral blood mononuclear cell

BMDM: Bone marrow-derived macrophages

Anti-PD-1: Programmed cell death protein 1

FMO: Fluorescence Minus One

The invention claimed is:

1. A method of treating a disease associated with the CSF-1R kinase signaling pathway in a mammal, comprising administering a therapeutically effective amount of the compound represented by formula (I) or a pharmaceutically acceptable salt thereof to the mammal in need of the treatment of the disease, wherein the disease associated with the CSF-1R kinase signaling pathway is CSF-1/CSF-1R-dependent leukemia, giant cell tumor of tendon sheath, or TAMs-enriched colorectal cancer, the TAMs-enriched colorectal cancer is a colorectal tumor that, at its invasive front, is determined to express any one of CD14, CD11c, CD68, CD11b, CSFIR, CSF1, CD115, CD206, PPARG, ARG1, CD163, CD301, Dectin-1, PDL2, Fizz1, CD204, PD-L1, Arginase-I, YM1, MGL2, Osteopontin, MMPs and CCR2 at 130% or more of the expression level of the corresponding surface marker in a peri-cancerous tissue, (I)

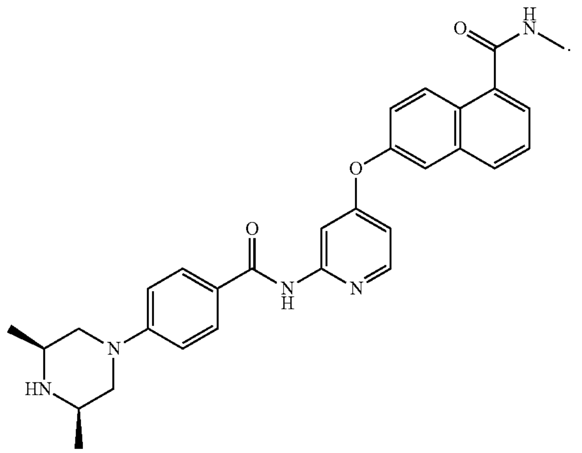

2. The method of claim 1, wherein the therapeutically effective amount is 0.01-2000 mg or 1-500 mg.

3. The method of claim 1, wherein the therapeutically effective amount of the compound represented by formula (I) or a pharmaceutically acceptable salt thereof is administered to the mammal by an administration mode selected from the group consisting of oral administration, intratumoral administration, rectal administration, parenteral administration and topical administration.

4. A method of treating or inhibiting a tumor in a mammal, comprising administering a therapeutically effective amount of the compound represented by formula (I) or a pharmaceutically acceptable salt thereof and an immune checkpoint drug to the mammal in need of the treatment or inhibition of the tumor, wherein the immune checkpoint drug is selected from the group consisting of an anti-PD-1 antibody and an anti-PD-L1 antibody, (I)

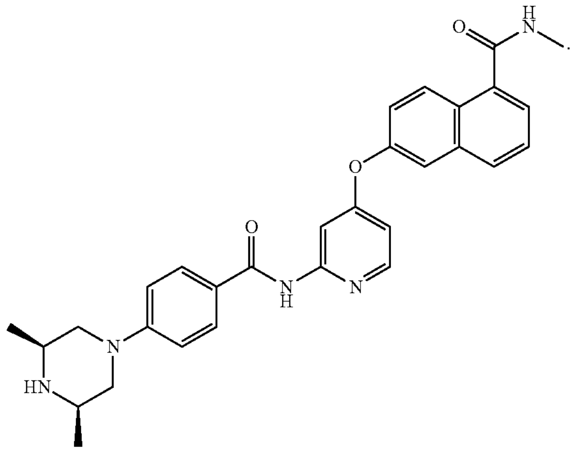

5. The method of claim 4, wherein the tumor is selected from the group consisting of colon cancer and colorectal cancer.

6. The method of claim 4, wherein the tumor is insensitive to the immune checkpoint drug.

7. The method of claim 4, wherein the therapeutically effective amount of the compound represented by formula (I) or a pharmaceutically acceptable salt thereof is 0.01-2000 mg or 1-500 mg.

8. The method of claim 4, wherein the therapeutically effective amount of the compound represented by formula (I) or a pharmaceutically acceptable salt thereof is administered to the mammal by an administration mode selected from the group consisting of oral administration, intratumoral administration, rectal administration, parenteral administration and topical administration.

* * * * *